Dec. 10, 1935. V. S. HILLOCK Plant Pat. 159
ROSE
Filed July 5, 1935
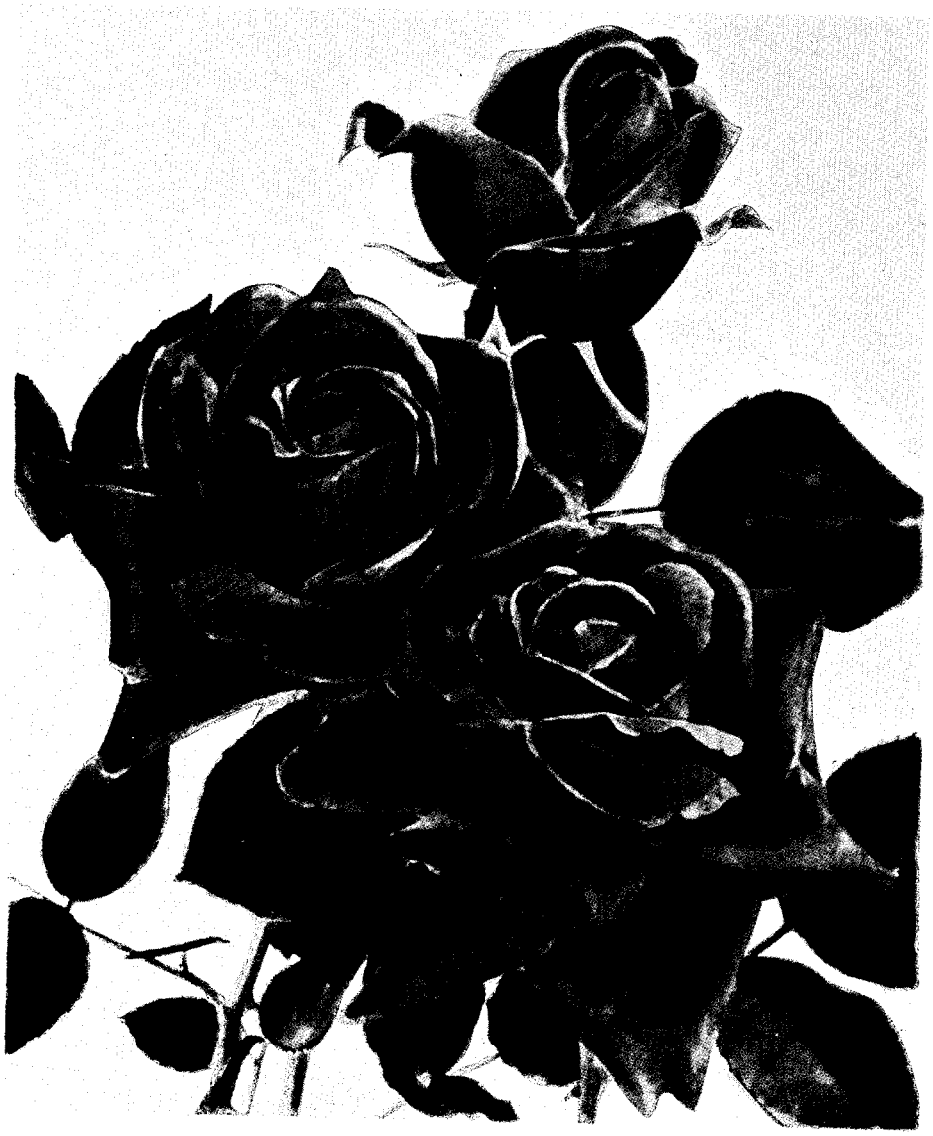
INVENTOR
Verne Stone Hillock
By Orville M. Kile
Plant Patent Agent Patented Dec. 10, 1935

UNITED STATES PATENT OFFICE

159

ROSE

Verne Stone Hillock, near Arlington, Tex.

Application July 5, 1935, Serial No. 29,991

1 Claim. (Cl. 47—61)

My present invention relates to improvements in hybrid tea roses. The object of this invention is to provide a new and distinct variety of rose of the type mentioned, having desirable and pleasing color qualities as well as other desirable characters which will hereinafter appear.

This new variety of rose was produced by crossing the variety Ami Quinard (see parent) with the variety Chateau de Clos Vougeot (pollen parent) by the usual cross-breeding methods. This work and the subsequent selection and testing was carried on by myself in Texas. Extensive asexual reproduction of this selected seedling has shown it to be a definitely established variety. Garden tests in several States during the years 1934 and 1935 further establish the distinctive and definitely fixed qualities of this new variety.

The accompanying illustration shows in full color and with approximate accuracy a partly opened bud and two flowers as well as foliage of this new variety. It must be understood, however, that there will be considerable variation in color and even in form of flower as between plants grown in southern latitudes and those grown in northern latitudes, also under different soil and temperature conditions. The illustrations shown represent the variety as grown in central Pennsylvania in mid-June, 1935.

*The flower*

The following description is based on observations made at Arlington, Texas, over a period of several years. Except when otherwise noted, observations relate to buds and blossoms of the first burst in springtime.

Blooming habit:

This rose tends to bloom in monthly bursts as is the habit of pure hybrid teas; but the duration of the bursts is such that they tend to overlap and an established bush under normal conditions is seldom entirely out of bloom during the entire summer except in mid-August.

Bud:

*Size.*—Medium.

*Form.*—Pointed.

*Weather effects.*—Is not affected by wet weather and is affected by heat only in the matter of color (see blossom).

*Color.*—Same as blossom.

*Sepals.*—Very finely serrated and are branched. They extend above the bud proper, forming a hood, which is usually short. The sepals curl back when the bud begins rapid growth, usually a day or two before the bud begins to unfurl. Sepals are permanent.

*Hips.*—Pear-shaped, slightly glandular, and of medium size.

*Peduncle.*—Of average length, slightly prickly, medium strong (holding the flower erect), and differs in color from the stem, being habitually slightly lighter or more "yellowish" in color.

*Opening.*—The bud opens well in all weathers. Thousands of buds have been observed, none of which have shown the slightest tendency to "ball."

Blossom:

*Size.*—Medium (three to four and one-half inches across).

*Borne.*—Singly and in sprays (several together).

*Stems.*—Some long to very long; some medium. The former are strong to very strong; the latter, medium. (In either event the flower is well held.)

*Form.*—An occasional blossom is cupped, with the center cleanly exposed but usually the blossom is high centered, with the center hidden in part by incurving petaloids. This form is held to the end.

*Petalage.*—The petals habitually number from twenty-five to thirty-five, according to the season.

*Color.*—One of the remarkable characters of this rose is its color which varies in accordance with the night temperatures. During spring and fall, when the nights are cool, the open blossom is habitually an even tone of garnet-maroon (between "garnet-brown" and "maroon" as shown in Ridgway's Color Standards and Nomenclature, Plate I), appearing almost black when viewed from a distance. The purple-black, apparent in Nigrette and markedly apparent in Crusader at certain seasons, is not present in this rose.

When this rose develops and opens on warm nights, the color is deep crimson without shadings. When night temperatures are greatly variable it often so happens that the bud opens partially on a cool night and completes its opening on a warm night following. Under such circumstances the open blossom displays two distinct colors, the outer petals being garnet-maroon, the inner petals glowing crimson.

However, when the temperature varies in the reverse order, the whole rose becomes garnet-maroon.

Petals:

*Appearance.*—The inner surface is markedly velvety at all seasons. The outer surface is smooth.

*Texture.*—Leathery without harshness. Not affected by wet weather. Not affected by heat except that it will burn in extreme heat, as any rose will do.

*Form.*—The inner petals are oval, the outer petals almost round (when pressed flat). The petals are slightly scalloped and frequently carry one notch at the outer extremity.

*Arrangement.*—Imbricated.

*Persistence.*—Drop off cleanly.

*Fragrance.*—Strong (same as Chateau de Clos Vougeot).

*Lastingness.*—The petals, and therefore the blossoms, are long-lasting both on the plant and when the blossom is cut. The lasting qualities of this rose as a cut flower are marked.

Genital organs:

*Stamens.*—The medium sized anthers are white with yellow edges. They are usually partially hidden by petaloids in more or less degree.

The medium-lengthed filaments are white and stand in one closely-set row around the styles.

*Pollen.*—Golden yellow.

*Styles.*—Bunched, medium length, wavy, and of uneven length.

*Stigmas.*—White inside. Outside lightly banded with carmine near terminus, the carmine extending in streaks of varying lengths down styles.

*Ovaries,*—Occasionally some protrude from calyx but in vast majority of cases all are tightly enclosed.

Fruit:

This variety is fertile with its own pollen.

*Form.*—Urn shaped, with flat head.

*Aspect.*—Smooth.

*Color at maturity.*—Orange-brown.

*Sepals.*—The sepals are permanent, sometimes recurving, sometimes standing straight.

*The plant*

Form:

Bush.

Growth:

Vigorous, upright, compact. This variety breaks freely from the bud, so freely that the bud-shoot need not be cut back in the growing field as is the usual practice. The plant throws shoot after shoot from the bud, or near the bud, each topped by an excellent blossom, the canes being in fact flower stems. These canes, or stems, then branch at the top into stems of lesser length. If permitted to grow without pruning, the plant becomes a compact, cylindrical plant of distinctive form.

Foliage:

*Leaflets.*—Usually five.

*Size.*—Medium.

*Quantity.*—Normal.

*Color.*—New foliage—bronzy to purple on the reverse, bronze and green on upper surface. Old foliage—normal green on both sides. (Popular color terms rather than definite color guide references).

*Shape.*—Pointed, at times almost lanceolate.

*Texture.*—Upper side—leathery and smooth. Under side—smooth except for ribs and veins. Ribs and veins—normal.

*Edge.*—Serrated.

*Serration.*—Double, medium depth.

*Leaf stem.*—Green. Broad, branched base, otherwise narrow. Prickles on the under side.

*Disease resistance.*—Resistant to black spot and mildew.

Wood:

*New wood.*—Light green with bronzy streaks and shadings.

*Old wood.*—Medium green, smooth bark.

Thorns:

*Quantity.*—Ordinary on both main stalks and laterals. Far less thorny than the average Pernetiana, slightly more thorny than the average hybrid-tea.

*Form.*—Narrow base. Thorns hooked slightly downward.

*Color when young.*—Very light green, almost transparent.

*Color when old.*—Brown.

*Position.*—Irregular.

*Prickles.*—None on canes and stems.

*Short needles.*—None on canes and stems.

*Comparisons*

The unopened bud of this new variety closely resembles in form the bud of Ami Quinard but the opened blossom discloses twice as many petals. The opened blossom closely resembles in form the blossom of Chateau de Clos Vougeot when the latter has not "quilled"; but the bush of this new variety grows sturdily upright while Chateau de Clos Vougeot sprawls.

This new variety at first glance somewhat resembles the variety Nigrette, yet in fact the two have practically no points in common. Nigrette is darker in color than this new variety, approaching purple whereas the new variety is garnet-maroon. (Nigrette does not show the interesting color combinations, including crimson, above described as characterizing this new variety under temperature changes). This new variety is a much more vigorous producer and develops larger buds and blossoms than does Nigrette.

Having thus disclosed my invention, I claim:

The variety of rose plant herein described and illustrated characterized particularly by its vigorous growth and prolific production of medium sized flowers of a distinctive garnet-maroon color under ordinary spring conditions, but when opening on warm nights displaying deep crimson shades or under some circumstances mixtures of these two colors.

VERNE STONE HILLOCK.